US008876711B2

(12) United States Patent
Lin et al.

(10) Patent No.: US 8,876,711 B2
(45) Date of Patent: Nov. 4, 2014

(54) VAGINAL DILATOR HAVING UPPER OR LOWER ACCESSORIAL BLADES OR SIDE BLADES

(75) Inventors: Jing Lin, Shanghai (CN); Xingxing Zhang, Shanghai (CN); Qianqian Wu, Shanghai (CN)

(73) Assignee: Shanghai Linjing Medical Equipment Co., Ltd., Shanghai (CN)

( * ) Notice: Subject to any disclaimer, the term of this patent is extended or adjusted under 35 U.S.C. 154(b) by 205 days.

(21) Appl. No.: 13/511,930

(22) PCT Filed: Jun. 24, 2011

(86) PCT No.: PCT/CN2011/076317
§ 371 (c)(1),
(2), (4) Date: May 24, 2012

(87) PCT Pub. No.: WO2012/006924
PCT Pub. Date: Jan. 19, 2012

(65) Prior Publication Data
US 2012/0232352 A1    Sep. 13, 2012

(30) Foreign Application Priority Data

Jul. 14, 2010   (CN) .......................... 2010 1 0227012
Jul. 14, 2010   (CN) .......................... 2010 1 0227014

(51) Int. Cl.
*A61B 1/32* (2006.01)
*A61B 17/42* (2006.01)
(52) U.S. Cl.
CPC .. *A61B 1/32* (2013.01); *A61B 17/42* (2013.01)
USPC ...................................... 600/220

(58) Field of Classification Search
USPC .................................. 600/184, 201, 219–226
See application file for complete search history.

(56) References Cited

U.S. PATENT DOCUMENTS 2,807,259 A * 9/1957 Guerriero ..................... 600/222
5,377,667 A * 1/1995 Patton et al. .................. 600/184
(Continued)

FOREIGN PATENT DOCUMENTS

CN    2417886    2/2001
CN    2531805    1/2003
(Continued)

OTHER PUBLICATIONS

International Search Report for international application No. PCT/CN2011/076317, dated Oct. 13, 2011 (6 pages).

*Primary Examiner* — Anu Ramana
(74) *Attorney, Agent, or Firm* — Hamre, Schumann, Mueller & Larson, P.C.

(57) ABSTRACT

A vaginal dilator having side blades or having upper and lower blades including accessorial blades is described. The vaginal dilator includes an upper blade, a pressing member, a lower blade and a handle. The upper and lower blades are connected by a pin. The pressing member is engaged with the handle by a first dilating fixation device. The vaginal dilator having side blades includes an arc-shaped movable locating sleeve rotationally connected with the upper blade. Each end of the sleeve is provided with a mounting base. The mounting base is provided with a joint cavity for receiving a side blade which can be retracted between the upper and lower blades. The back portion of the side blade is provided with a second dilating fixation device engaged with the back end of the upper blade or a locating buckle of the mounting base.

16 Claims, 6 Drawing Sheets

(56) References Cited

U.S. PATENT DOCUMENTS

| | | | |
|---|---|---|---|
| 5,509,893 A * | 4/1996 | Pracas | 600/224 |
| 5,681,265 A * | 10/1997 | Maeda et al. | 600/219 |
| 6,024,696 A | 2/2000 | Hoftman et al. | |
| 6,074,343 A * | 6/2000 | Nathanson et al. | 600/214 |
| 6,432,048 B1 | 8/2002 | Francois | |

FOREIGN PATENT DOCUMENTS

| | | |
|---|---|---|
| CN | 200957079 | 10/2007 |
| CN | 200991225 | 12/2007 |
| CN | 201061667 | 5/2008 |
| CN | 101366991 | 2/2009 |
| CN | 201192334 | 2/2009 |
| CN | 101869735 | 10/2010 |
| CN | 101869736 | 10/2010 |
| CN | 201735046 | 2/2011 |
| CN | 201735047 | 2/2011 |
| WO | 99/12466 | 3/1999 |

\* cited by examiner

VAGINAL DILATOR HAVING UPPER OR LOWER ACCESSORIAL BLADES OR SIDE BLADES

This PCT international application claims the priorities of Chinese invention patent applications No. 201010227014.9 and No. 201010227012.X filed on Jul. 14, 2010, the contents disclosed in which are incorporated hereinto by reference.

FIELD

The present invention relates to a vaginal dilator, particularly to a vaginal dilator having side blades or having upper and lower blades comprising accessorial blades.

BACKGROUND

A vaginal dilator is a conventional examination and operation instrument in gynecology and obstetrics for exposing examination or operation areas. A conventional vaginal dilator comprises an upper blade and a lower blade, which can be opened and closed and have a duckbilled shape. Keeping upper and lower blades dilated to a certain angle by means of a locating device or a dilating fixation device on the dilator, doctors can watch, examine and operate through the sight range, which is obtained by dilating the upper and lower blades. In fact, it reduces the exposed extent, leading to difficulty for examination or operation that the upper and lower blades are restricted by their own widths. The vaginal walls between two sides of the upper and lower blades backfill the dilated areas. It will bring more pain to a patient and also increase backfill of the vaginal walls that the dilated angle between the upper blade and the lower blade is increased, therefore, this is not a good countermeasure.

Directing at the above drawbacks in the prior art, the PCT international application No. PCT/AU98/00737 has disclosed a speculum. The solution suggested by this application is that a speculum comprises a main body with two dilating fingers 14A, 14B, which are connected at their respective proximal ends to the main body, a further dilating finger 28 extends between the above-mentioned fingers and is fixed to the main body, an actuator is pivotally connected to the main body, the actuator is formed with a dilating finger 70 which faces the fixed finger 28 locating between the fingers 14A and 14B. When the actuator is pivoted, this finger immediately starts to pivot away from the other fingers. After the actuator rotates a certain degree, it comes into contact with the inside of the fingers 14 near their proximal ends, so as to cause the distal ends of those fingers to move away from each other, Fingers 14A and 14B are hinged around a canted hinge axis so that they move in a combined motion upward and sideways when they are abutted by the actuator. Chinese patent No. 200620133849.7 has disclosed "a speculum having four blades used in gynecology." The solution suggested is that the four blades are rotatably fixed on a handle in uniform distribution by means of pivots, which are connected to circle holes located on an upper portion of the handle, the simultaneous opening or closing of the four blades is performed by a controlling device provided by this patent. Chinese patent No. 200820080747.2 has disclosed "a speculum having several blades used in gynecology." The difference from the former is that there may be three or four blades, but the means of connection to the handle is the same. Chinese patent No. 200620172721.1 has disclosed a "speculum for uterine neck having multiple pages." The solution of the speculum disclosed in this patent is different from the ones in the above three patents, and includes an upper page of duckbill and a lower page of duckbill, and a pivot provided on a side of the lower page of duckbill and a rotating page connecting to the lower page of duckbill, so as to realize the vaginal expansion in three directions upward, downward and sideward.

The above four patents have made contributions to overcome the drawbacks in the prior art. However, there is a drawback existing in the former three patents that the side blades are all arranged on outside of the upper and lower blades and cannot be retracted into inside of the upper and lower blades, thereby causing pain to a patient when a dilator or speculum is inserted into a vagina; although the fourth patent has made up the drawback of the former three patents to a certain extent by providing a side blade inside a lower blade, there is a drawback of having only a side blade which acts only as an obstruction rather than dilating vaginal walls when used.

On the other hand, with rapid popularization of the electronic colposcopes, quite a number of women patients who get diseases of uterine neck need employing a loop electrosurgical excision procedure (LEEP) for cervical cancer precursor. A harmful smoke with an empyreumatic and unpleasant smell, which stimulates the throat, can generate when performing this operation, which affects the health of doctor and patient, and meanwhile obscures sight line of doctor.

Chinese patent application No. 200810107219.6 has disclosed "a disposable vaginal dilator having two protecting blades with discharging smoke type", which includes upper and lower blades, a smoke pipe, which communicates with a smoke device, is provided on an inside of the upper blade, the upper and lower blades are provided with protecting wings, which can be ones with a type of elastic silicon sleeves, or a type of elastic aliform or a folding type similar to accordion. The wings act as barriers for preventing exposed vaginal walls between upper wing and lower wing from risk of suffering scorching hot and can not play the role of dilating vaginal walls, when performing the operation with the LEEP. The upper wing is provided with a smoke pipe, the smoke pipe is a pipe sealed around except both ends thereof being communicating with each other and does not have a channel cover, saying nothing of opening the channel cover. An operator can not install mini-instruments, such as LED, camera, etc., under looking in the eye.

Chinese patent application No. 00232603.5 has disclosed a "disposable vaginal speculum with a fasten-closing type", in which an electric light source with an outgoing wire and a joint is provided on inside of an upper blade near the root thereof, the electric light source can connect to the lamp socket by screw, and a pipe for eliminating smoke is provided on a lower blade and a handle, Wherein the pipe for eliminating smoke can be made be integrated with the lower blade, besides that lower end of the smoke pipe connects to a negative pressure suction tube by a hosepipe, or a hard elbow can be fixed on the lower blade. There is a drawback for it that the electric light source with the outgoing wire and the joint present an unsafe risk as regards medical apparatus, even if a part of the source is not within inside of the sealed pipe, and does not possess the clinical applicability. If the electric light source is entirely installed within the pipe, because the pipe described in this patent and the pipe for eliminating smoke are both sealed around them rather than a close match of a channel cover which can be opened and closed with a channel of the pipe, up to now, such a long and bended pipe for eliminating smoke on the lower blade can not be made by means of a plastics mould and present the difficulty of demoulding, so as to limit the practical applicability.

Chinese patent application No. 200720038815.4 has disclosed a "vaginal dilator with a structure of discharging smoke", the inside of upper duckbill blade is provided with a pipe for discharging smoke, and several through-holes are arranged on body of the pipe for discharging smoke, The through-holes are arranged on base of front end of the body of the pipe for discharging smoke, the distal end of which extends to tail of the duckbill. Although the structure described in this patent is more improved in comparison with the one having two pipes being sealed around them in that several through-holes are arranged on the body of the pipe for eliminating smoke, i.e., each of the through-holes is arranged at a distance on the pipe for discharging smoke, instead of the channel cover, which can be opened entirely, the "several through-holes" arranged on the vaginal dilator with the structure of discharging smoke can only be used for discharging smoke, does not possess the functions that the whole channel cover can be opened and the operator can rapidly and accurately install devices such as LED lamp, camera, etc., under looking in the eye, so as to increase a lot of clinical utility functions of the vaginal dilator, furthermore, there is only one pipe for discharging smoke, this is adverse to rapidly discharge toxic smoke, and also can not achieve the function and effect that the several pipe channels can discharge smoke in cooperation.

Similarly, U.S. Pat. No. 6,432,048B1 has disclosed a vaginal dilator with a lateral walls retractor, the function of the lateral walls retractor is that the vaginal dilator is dragged under condition of keeping vaginal tissue loose in a lateral direction, and the retractor does not form a channel for discharging smoke.

in another aspect, with development of the clinical medicine, it is required that the positions to be examined and performed operations can be more clearly observed and are supplied with real-time images to meet needs of diagnosis and teaching, for this purpose, it is necessary to be required that a channel and a channel cover for installing devices of illumination or camera, etc, are provided within the vaginal dilator and openings are arranged on the front and back ends, in other words, Only when possessing the three essential elements, i.e., a channel, a channel cover and openings which are arranged on the front and back ends, it can be realized that the devices of illumination, camera, etc, can be installed accurately, reliably, rapidly and conveniently, and the clinic uses can be safe and effective.

Furthermore, up to now, there has been no a kind of vaginal dilator having side blades or upper and lower blades having accessorial blades, in which illumination as well as camera devices, etc, can be installed by providing channel, channel cover and openings being arranged on front and back ends thereof and which can discharge smoke with multi-purpose for one pipe, or simultaneous use for several pipes, or single use for each of the pipes.

SUMMARY

The object of the present invention is to provide a vaginal dilator which can achieve that two side blades can be retracted into between the upper blade and the lower blade before the side blades enter into the vagina, so as to avoid the side blades being exposed outside the upper and lower blades, which can lead to harm and pain of the vaginal walls and having no clinical safe. When used, each of the vaginal walls can be dilated effectively so as to obtain a necessary clinical field of vision for facilitating and more rapidly discharging harmful smoke produced during operations and which can be provided with a channel for installing illumination or camera devices, etc., a channel cover and a slot, which is arranged on an edge of the channel body, for embedding the channel cover.

To achieve the above-mentioned object, according to an aspect of the present invention, a vaginal dilator having two side blades is provided. The vaginal dilator includes an upper blade; a pressing member integrated with the upper blade and extending downward from the upper blade in a direction with an obtuse-angle relative to it; a lower blade; and a handle integrated with the lower blade and extending downward from the lower blade, in a direction with an approximate right-angle relative to it, wherein the upper and lower blades are connected by pins, the pressing member and the handle are engageable by a first dilating fixation device, characterized in that said vaginal dilator further includes a circular-arc movable locating sleeve, wherein two ends of the locating sleeve are connected to the two sides of the back end of the upper blade with pins of the movable locating sleeve, a mounting base provided on each end of the locating sleeve, wherein the mounting base includes a mounting hole for receiving a joint axle member of the side blade, and wherein the side blades are pivotally retractable between the upper blade and the lower blade, a back portion of each side blade including a second dilating fixation device capable of holding the side blades open from each other, the back portion of each side blade configured to engage with the upper blade.

More perfectly, each of the side blades has a front portion and a back portion. The front portion is longer than the back portion. Between the back portion and the front portion there is a middle portion protruding outwardly, and an insert extending radially inwardly being provided in the inner side of the middle portion near the top of the middle portion.

More perfectly, said side blades have at least one channel, the inner side of the front end thereof is provided with at least an opening being communicated with the channel.

More perfectly, said channel is composed of a channel body and a channel cover.

More perfectly, a slot used for embedding the channel cover is formed at edges of the channel body.

More perfectly, said pins of the movable locating sleeve drive the side blades to rotate upward or downward through the rotation of the shaft-hole of the upper blade, or move the side blades so as to regulate the upper and lower positions thereof through rotation of the joint structure together with the movable locating sleeve.

More perfectly, a limiting slot is arranged on the middle portion at the back end of upper blade, a limit block is arranged correspondingly at inside of the middle portion of the movable locating sleeve, the movable locating sleeve and the side blades can limit through the limit block the maximum range, within which the movable locating sleeve and the side blades rotate downward.

More perfectly, said first dilating fixation device comprises at least a locating hook and locating buckle respectively on the pressing member and the handle, and the locating hook and the locating buckle can be interchangeable.

More perfectly, said first dilating fixation device comprises a locating plate, which is arranged on the pressing member and has an arc-shaped slot, and can rotate around a pin, which is as a rotating center and connects the upper and lower blades. The handle is provided with a locating rod, which is attached a nut and passes through the arc-shaped slot on the locating plate.

More perfectly, said second dilating fixation device comprises at least a locating hook on the back portions of the side blades, and at least a locating buckle on the back end of the upper blade or the mounting bases, and the locating hooks and locating buckles can be interchangeable.

More perfectly, said second dilating fixation device comprises a screw, which is provided on inside of the back end of the side blade and extends inward, the screw passes through the locating buckle, which protrudes upward from the back end of the upper blade or the mounting base, the screw and locating buckle are fixed by a nut. Or the screw passes through a locating plate provided on the back end of the upper blade, the locating plate having an arc-shaped slot and can be rotated around a pin which is as a rotating center and connects the upper and lower blades, and a nut being provided on the screw.

More perfectly, each of said blades comprises a front portion and a back portion, between which there is a middle portion being recessed inward, and appears in a bent strip entirely, a joint axle member, which extends radially-inward and protrudes inward, is provided on the inside of the middle portion near the top, the joint axle member and the joint cavity can be pivotally engaged.

More perfectly, the front-middle portion of each of the side blades appears in an inward arc shape, the front end of the front portion is substantially flat and straight.

More perfectly, said front portion of each of the side blades appears in a duckbilled shape.

More perfectly, the front portion of each of the side blades appears in a rounded shape.

After the end of examination and operation, the dilating fixation device, which engages the locating buckles, which are arranged on back portion of the side blades and the back end of the upper blade or on the mounting bases, is loosened, the left and right blades are retracted into insides of the upper and lower blades, then the first dilating fixation device is disengaged the upper and lower blades are retracted and then the vaginal dilator having side blades is taken out from vagina.

According to another aspect of the present invention, a vaginal dilator having upper and lower blades comprising accessorial blades is provided. The vaginal dilator includes an upper blade and a pressing member integrated with the upper blade and extending downward from a back end thereof along a direction with obtuse-angle relative to each other, a lower blade, and a handle integrated with the lower blade and extending downward from a back end of the lower blade in a direction with an approximate right-angle relative to each other, two sides of the back ends of the upper and lower blades are connected by pins, the pressing member and the handle are engageable to hold the upper and lower blades open from each other by a dilating fixation device; upper and lower accessorial blades provided on inner sides of the upper and lower blades respectively, wherein each of the upper and lower accessorial blades is provided with a channel including a channel body and a channel cover engaged with the channel body, wherein the edges of the channel body form a slot into which the channel cover can be embedded, said channel including at least one opening facing the vagina or at least one hole facing the inner side of the upper blade and lower blade.

After the end of examination and operation, the dilating fixation device is disengaged, the upper and lower blades are retracted, and then the vaginal dilator having upper and lower blades comprising accessorial blades is taken out from the vagina.

It should be pointed out that the technicians in the art can easily appreciate that the above technical solution also can be applied to a vaginal dilator comprising upper and lower and side blades, though the above technical solution only refers to a vaginal dilator having upper and lower blades.

The side blades of the present invention can be designed as a left blade and a right blade. A left side blade or a right side blade, or both side blades can be installed based on the clinical need; and the left and right side blades can be added with an additional upper accessorial blade, or a lower blade, or both the upper and lower accessorial blades, which are installed based on the clinical need.

Adopting the vaginal dilators according to the above-mentioned solutions of the present invention, when using, the vaginal dilator is inserted into the vagina under the condition that the upper and lower blades are closed and the side blades are retracted between the upper and lower blades, the upper and lower blades are opened to a needed field of vision by controlling the handle and pressing member. The extent of the field of vision is kept through the first dilating fixation device. The back ends of the left and right side blades are controlled to move in opposite direction so as to dilate the two side blades up to a needed field of vision. The second dilating fixation device engages the locating buckles, which are arranged on a back portion of the side blades and back end of the upper blade or on the mounting bases, at this moment, observation and examination and/or operation on vagina, cervix can be performed through the field of vision, which is obtained by dilating the upper and lower blades and the left and right blades.

Because the vaginal dilator of the present invention is provided with channels on the side blades or accessorial blades of the upper and lower blades, the invention provides the possibility that different use requirements can be achieved.

When the operation on vagina or cervix is performed by adopting an ultrahigh-frequency wave bistoury, the produced smoke can pass through the openings, which are arranged on insides of the left blade and/or the right side blade, and/or the openings, which are arranged on sides of upper and lower accessorial blades, pass through the pipes, which are installed in the channels and can be discharged through the negative pressure device connecting with the back end of the pipes. It is obvious that in comparison with the prior art, the vaginal dilator having upper and lower blades comprising accessorial blades according to the present invention is provided with additional channels for discharging smoke, which are arranged inside the left and right blades and lower accessorial blade, so that the smoke discharge is increased and accelerated, more availing the health of doctor and patient.

When examination and operation are performed by adopting the vaginal dilator according to prior art, the observation and operation are conducted by means a high-power illumination locating at outside site, therefore, the illumination to examine and operate on deeper positions within the vagina is poor. According to the vaginal dilator of the present invention, the side blades are provided with channels, the upper accessorial blade and lower accessorial blade are respectively provided with the channels, which are composed of channel covers and channels, or are composed of channel bodies, channel covers and slots, which are formed by edges of the channel bodies and are used for embedding the channel cover, therefore, the whole channels can be entirely exposed so long as the channels are opened, so that the illumination device, such as LED, can be very conveniently and accurately installed at the openings, which locates in the insides of the left side blade and/or right side blade and/or in the insides of the upper accessorial blade and/or the lower accessorial blade, the power supply lines can be pulled out and connect to a power source under look in the eye of the operator through channels, which are arranged inside the side blades and/or the upper accessorial blade and/or the lower accessorial blade and are exposed entirely. After installing, the channels are closed by the channel covers, so the examination and operation on deeper positions of vagina can be performed under the better illumination condition, because power source, power supply lines and devices are all installed within the channels, the conditions for examination and operation are improved and the safety and reliability are ensured.

Similar to the above-mentioned principle, because a design for the channel covers is adopted, the vaginal dilator of the present invention can be installed with a camera at the opening of the channels, which are entirely exposed and are arranged in front ends or insides of the left side blade and/or the right side blade or upper accessorial blade and/or lower accessorial blade. It is possible to provide real time the images of the positions to be examined or operated, whether adopting wire transmission or wireless transmission. This can meet the needs and requirements in contemporary medicine to provide real-time images, and the conditions necessary for clinic diagnosis, even remote consultation and teaching.

Just because a well design for the channel covers has been adopted, the channel covers can be opened to meet the requirements that the illumination or camera devices can be installed accurately, conveniently and rapidly under look in the eye of the operator and smoke can be discharged simultaneously after the channel covers and the channels are sealed. The multiple purposes can be achieved.

Also just because a well design for the channel covers has been adopted, the upper and lower accessorial blades and the side blades, which are so long and bended, can be made of common plastics or degradation materials and can easily achieve demolding. The vaginal dilator can be disposable and possesses significant importance that the cross infection of iatrogenic diseases can be completely eradicated when the vaginal dilator is applied to operations, which are completed by adopting LEEP in early lesion of cervical cancer.

Furthermore, the upper accessorial blade can adopt a hook, which is provided in front of the back portion of the upper accessorial blade, the hook for upper accessorial blade is buckled into the limiting slot on the middle portion of the back end of the upper accessorial blade so as to be fixed detachably; a fixation buckle is provided at the back of the back portion of the lower accessorial blade, the buckle for the lower accessorial blade can be buckled into a limiting slot on the middle portion of the back end of the lower blade so as to be fixed detachably. The benefit of the detachable fixation above-mentioned lies in that the installation can be conducted immediately according to clinic requirements.

The present invention possesses prodigious flexibility and adaptability because the back portions of the side blades are provided with second dilating fixation devices, which engage the locating buckles, which are arranged on the back ends or the mounting bases, the left and right side blades can be installed with a left side blade or right side blade or both the left and right ones according to needs, furthermore, the left and right side blades can add an upper accessorial blade or a lower accessorial blade or both the upper and lower ones, which are installed according to the clinic needs.

Obviously, the vaginal dilator according to the present invention has overcome the drawbacks existing in the prior art, can achieve the required dilation in clinic when the dilator is inserted into vagina per the height and width, which are as same as or similar to the height and width of the dilator, which is provided only with an upper blade and a lower blade, and can reduce pain of a patient, and the accessorial blades to be provided can be hidden within the insides of the upper and lower blades, so it does not bring pain to the patient because the accessorial blades are added so as to increase the overall dimension of the dilator or does not increase the cost of production The vaginal dilator according to the present invention also possesses the advantages that the structure is simple, the manufacture is easy and the cost is low.

BRIEF DESCRIPTION OF THE DRAWINGS

The above and other objects and advantages of the vaginal dilator having side blades or upper and lower blades according to the present invention will be more clear and apparent through the following detailed description of embodiments in combination with the drawings, wherein.

DETAILED DESCRIPTION

An embodiment of a vaginal dilator according to the present invention is described in combination with the drawings as follows. First referring to FIGS. 1 and 2, a vaginal dilator having side blades includes: an upper blade 1; a pressing member 3 integrated with the upper blade 1 and extending downward from the upper blade in a direction of an obtuse-angle; and a handle 4 integrated with the lower blade 2 and extending downward from the lower blade 2 in an approximate right-angle relative to each other, the upper and lower blades 1, 2 are connected by pins 5. Therefore, upper blade 1 and lower blade 2 can be opened and closed by controlling the pressing member 3.

Figure 1:
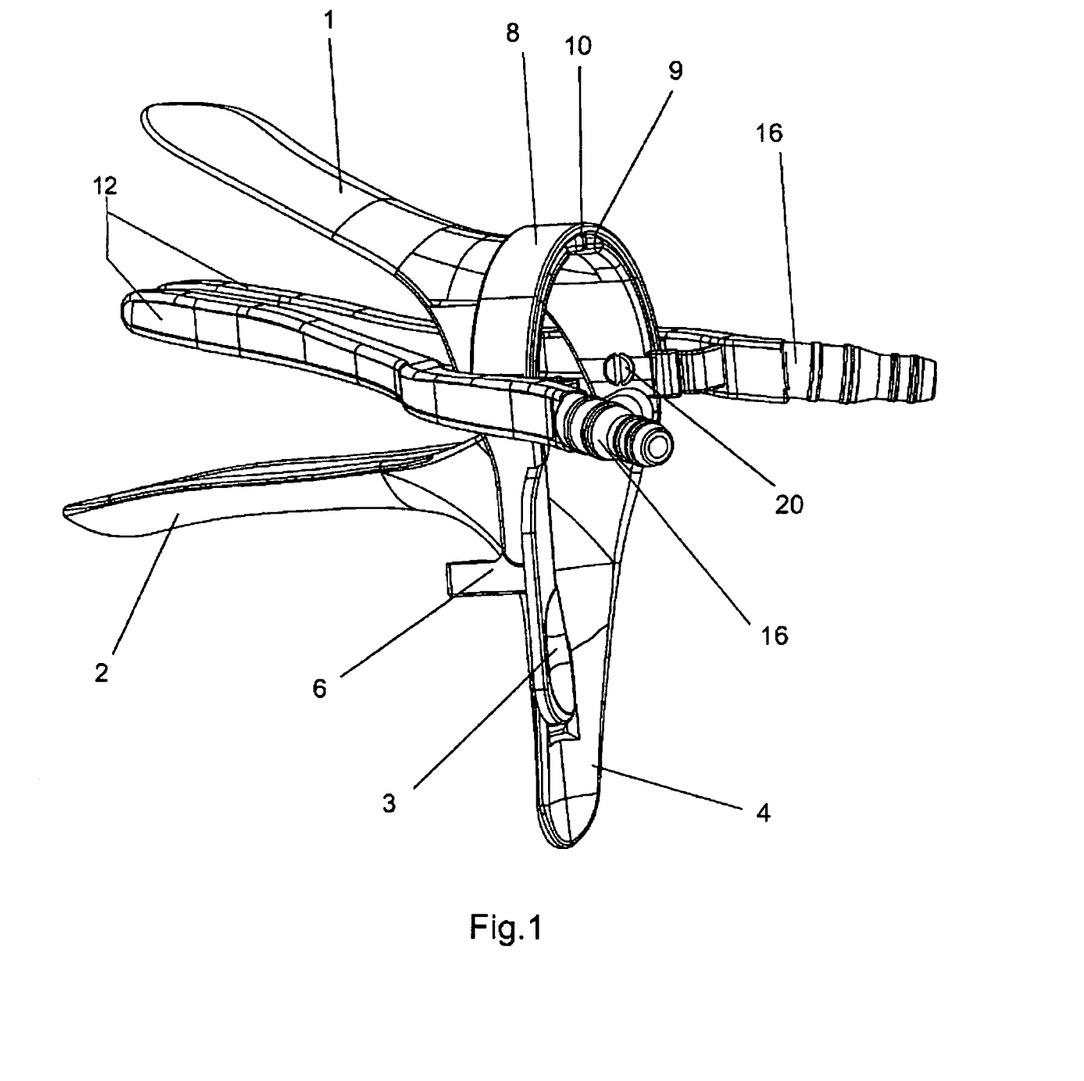
FIG. 1 is a perspective view from front sighting, showing an embodiment of a vaginal dilator having side blades according to the present invention.
Figure 2:
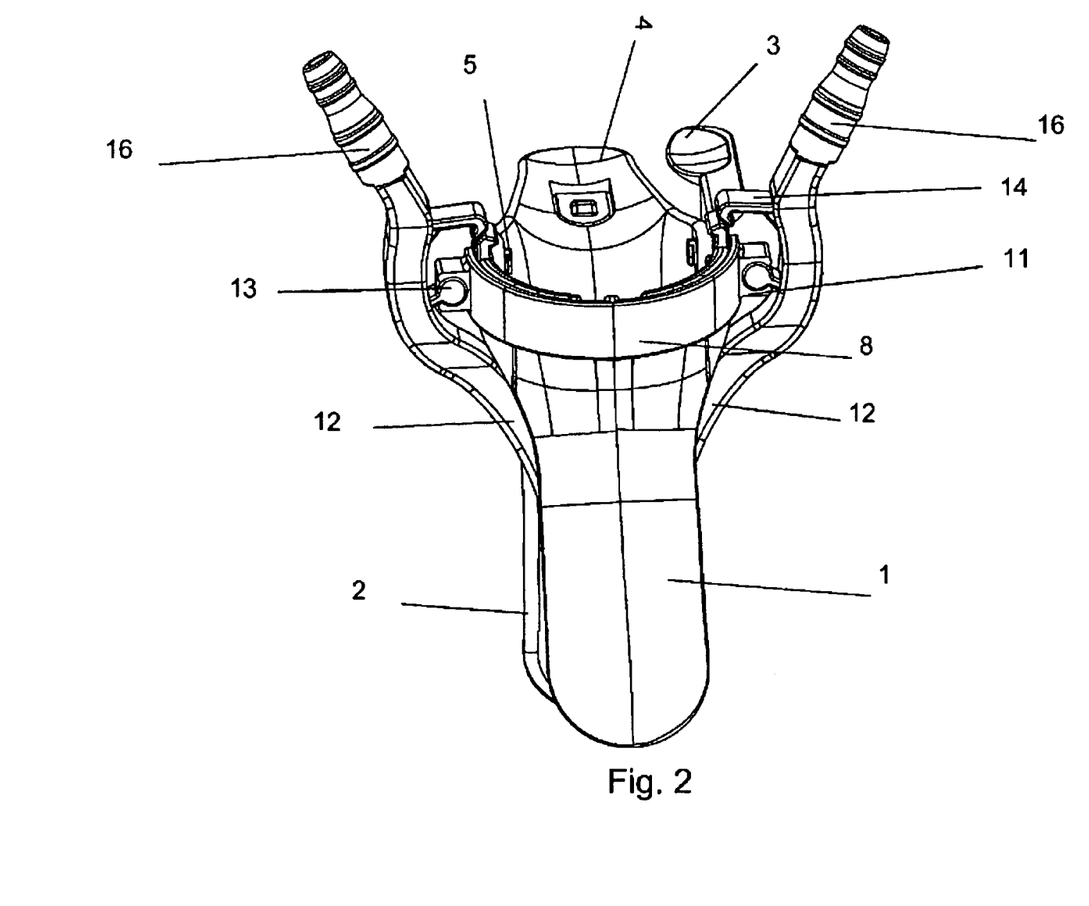
FIG. 2 is a perspective view from top sighting of the vaginal dilator having side blades shown in FIG. 1.

A first dilating fixation device is engageable to hold the upper and lower blades 1 and 2 open from each other. The first dilating fixation device further includes a locating hook plate which locates on a front end of the pressing member 3 and extends to the left direction as shown in FIG. 1. A locating hook is situated on an inside of the locating hook plate 6, and a locating buckle (not shown), which locates on a handle 3 and position of which corresponds to the locating hook plate. According to another embodiment of the present invention, the first dilating fixation device, which locates between upper and lower blades, comprises a locating plate with an arc-shaped slot, which is arranged on the pressing member and rotates around the pin 5, as a rotating center, the handle is provided with a locating rod with a nut passing through the arc-shaped slot on the locating plate.

A movable locating sleeve 8 with a circular arc shape is arranged on the outside of the back end of upper blade 1, and rotatably connects with the shaft hole of the upper blade 1 through the pins 20 on the two ends thereof, wherein, a limiting slot is arranged on the middle portion at the back end of said upper blade 1, a limit block 10, the position of which corresponds to the limiting slot, is arranged at inside of the movable locating sleeve 8.

Figure 3:
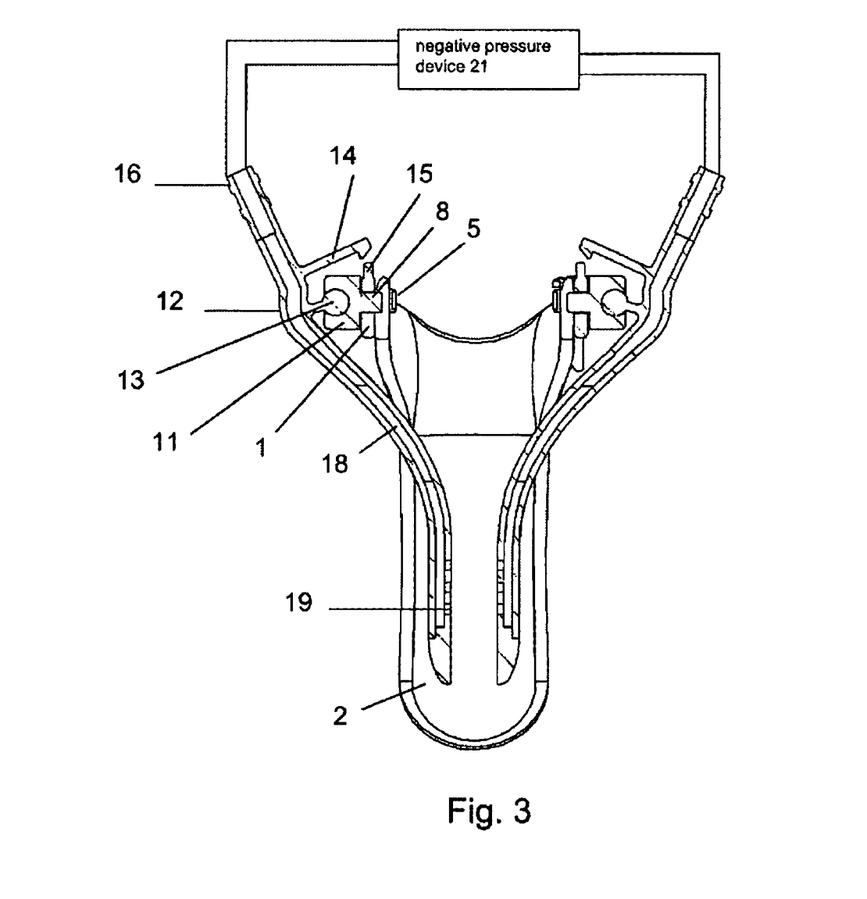
FIG. 3 is a sectional view of the vaginal dilator having side blades shown in FIG. 2.

Referring to FIG. 3, each of outsides of the both ends of the movable locating sleeve 8 is provided with a mounting base 11 respectively, At least a side blade is provided in the present invention. In this embodiment, there are two side blades, which are provided as a left blade and a right blade, which are of the same structure and arranged symmetrically, said joint structure includes a joint axle member 13, which is formed on the middle and upper portion of the side blade 12, and a joint cavity, which is formed on each of the mounting bases 11, the joint axle member 13 and the joint cavities are matched each other so that the side blades 12 pivot relatively to the mounting bases.

According to an embodiment of the present invention, each of said side blades 12 has a front portion, a back portion, and a middle portion between the front and back portions. The middle portion is concave inward. A joint axle member, is provided on the middle portion near the front portion. The joint axle member extends radially inward from the middle portion and protrudes inward. The joint axle member and the joint cavity can be pivotally engaged.

The front portion of each of the side blades 12 appears in an arc shape. According to another embodiment of the present invention, said front portion of each of the side blades appears in a duckbilled shape. According to yet another embodiment, the front portion of each of the side blades appears in a rounded shape.

The vaginal dilator having side blades according to the present invention, a second dilating fixation device is provided between inside of the back portion of each of the side blades and the back ends of the upper blade or the mounting bases (not shown in the drawings). The second dilating fixation device is used for regulating and fixing the opening extent of the side blades. According to an embodiment of the present invention, a locating hook 14, which extends inward, is provided on inside of the back portion of each of the side blades 12. Accordingly, a locating buckle 15, which engages with the locating hook 14, is provided on the back end of the upper blade 1 or the mounting base. The amount of the locating hook is at least one or more than one used for regulating the left-right dilating distance of the side blades, when the locating hook 14 and the locating buckle 15 are engaged, the opening condition of the left and right side blades 12 is fixed.

According to a second dilating fixation device of another embodiment of the present invention, a screw, which extends inward, is provided on inside of the back end of each of the side blade 12, the screw passes through the upper blade, the back end is provided with a locating plate, which has a slot with an arc shape and can be rotated around a pin 20 as a rotating center, and a nut is provided on the screw. The side blades and upper blade are connected firmly by screwing the nut, so as to achieve the dilation and fixation of the side blades.

It is not difficult to understand that the back ends of the side blades 12 are actually the handles for controlling the side blades 12 to operate.

According to an embodiment of the present invention, there is a channel 18 inside each of the side blades 12. At least one opening, which is in communication with the channels, is provided on each side of the front end of side blades 12, except the outer side respectively thereof, such as an inner side, upper side, or lower side. It is not useful to provide an opening of the channel on the outer side because the outer side of the channel will contact the vaginal wall when the side blades are expanded.

In the side blades the channels can be, or not, provided with channel cover. If channel covers are provided on the channels, then the edge of the channel body can best have a slot used for embedding the channel cover into it, in order to achieve the seal-connection.

In a vaginal dilator having upper and lower blades comprising accessorial blades, the channel of each of the accessorial blades is composed of a channel body and an accessorial blade cover thereon. The edges of the channel, body are formed with a slot, into which the channel cover can be embedded, so as to rapidly, accurately and safely conduct, for example, installing LED and laying power lines and simultaneously exhaust smoke.

According to an embodiment of the present invention, the back end of each of the side blades can be formed as pipe joints 16 when the channels are used for exhausting smoke, for easier connection to a negative pressure device 21 through hoses (including a single-pass, double-pass, three-pass and multi-purpose hoses), as shown in FIG. 3.

A vaginal dilator having upper and lower blades comprising accessorial blades according to another embodiment of the present invention will be described in combination with drawings as follows. First referring to FIG. 4, the vaginal dilator includes: an upper blade 1, a pressing member 3 integrated with the upper blade 1 and extending downward from a back end thereof along an obtuse-angle relative to each other; a lower blade 2, a handle 4, integrated with the lower blade 2 and extending downward along a back end thereof in an approximate right-angle relative to each other, rear portions of the upper and lower blades 1 and 2 are connected by pins 5, therefore, the upper blade 1 and lower blade 2 can be opened and closed by controlling the pressing member 3.

A dilating fixation device for fixing dilating condition of upper blade 1 and lower blade 2 further includes: a locating hook plate, which locates on the front end of the pressing member 3 and extends to the left side direction shown in FIG. 1, a locating hook 6 locates at inside of the locating hook plate, and a locating buckle, which is provided on the handle 4 and corresponds to the position of the locating hook 6 (not shown). A dilating fixation device according to another embodiment of the present invention, the dilating fixation device locating between the upper blade and lower blade includes: a locating plate having a slot with arc shape, which rotates around a pin 5 as a rotating center, is provided on the pressing member, a locating rod, which is provided with a nut and on the handle and passes through the slot with arc shape on the locating plate.

Figure 4:
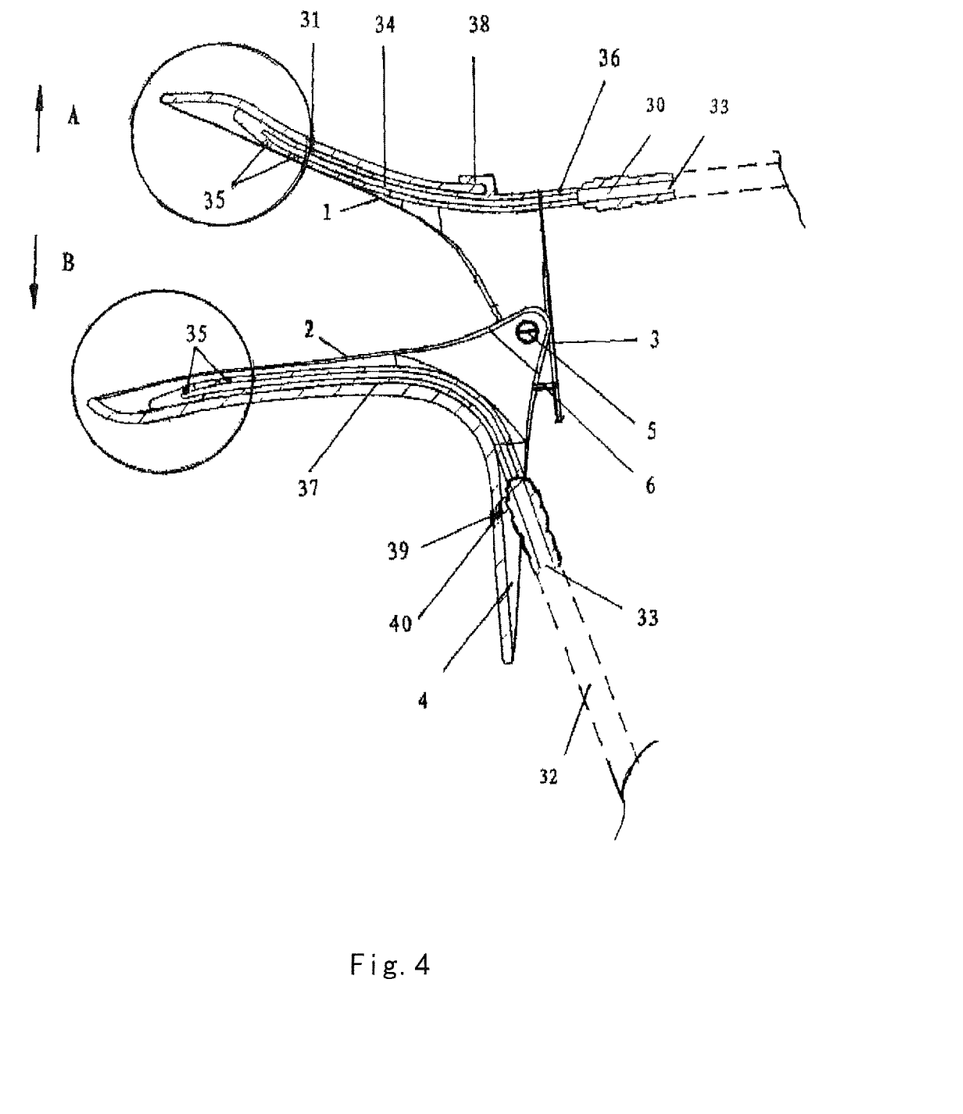
FIG. 4 is a sectional view of another embodiment of a vaginal dilator having upper and lower blades comprising accessorial blades according to the present invention.
Figure 5:
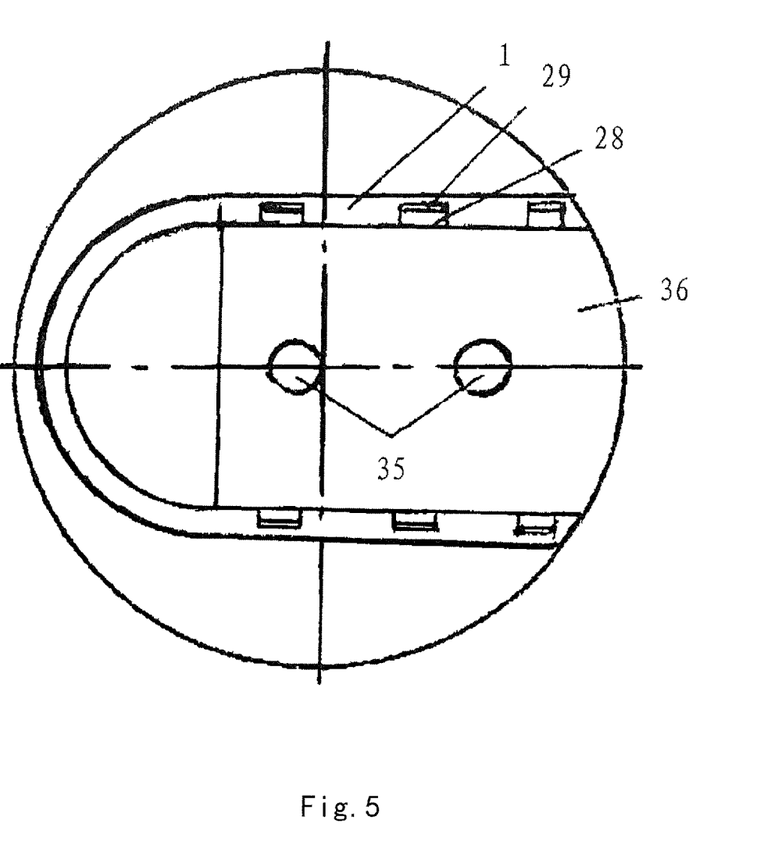
FIG. 5 is an enlarged view from a direction shown in FIG. 4.
Figure 6:
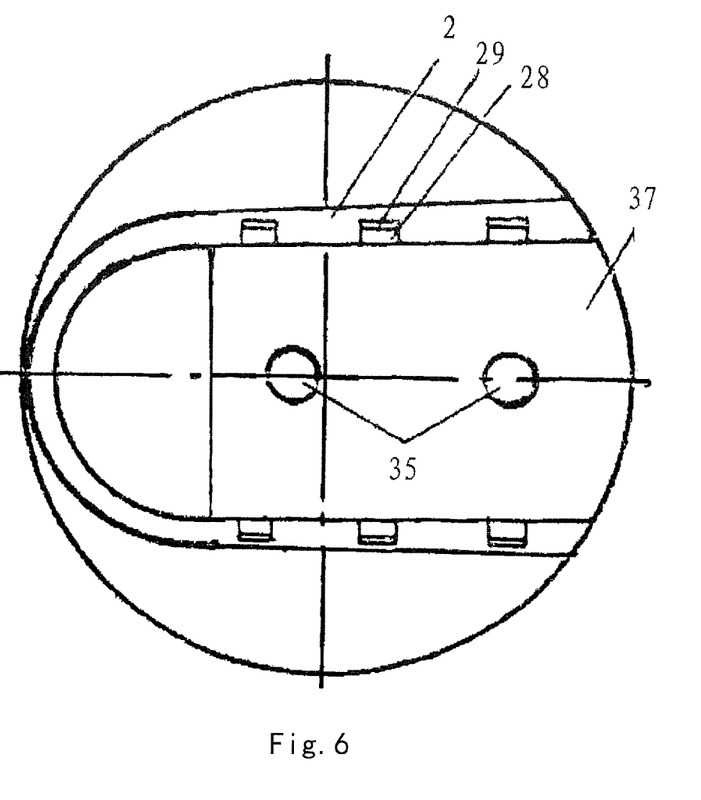
FIG. 6 is an enlarged view from B direction shown in FIG. 40

Continuing to refer to FIG. 4, the front ends of the upper accessorial blade 36 and lower accessorial blade 37 are "invisibly" provide on the inside of the upper and lower blades 1 and 2. Wherein a plurality of bumps 28 arranged on outer edges of the upper and lower accessorial blades 36 and 37, accordingly, a plurality of grooves 29 are arranged on the outer edges of insides of the upper and lower blades 1 and 2 at the positions corresponding to the bumps 28, fit of the bumps 28 and grooves 29 makes the upper and lower accessorial blades 36 and 37 be integrated with the upper and lower blades respectively (see FIGS. 5 and 6). According to an embodiment of the present invention, each outer edge of the upper and lower blades 36 and 37 is provided with a plurality of snaps, correspondingly, each of the upper and lower blades 1 and 2 is provided with snapper seats for receiving said snaps, so as to respectively connect the upper and lower accessorial blades 36 and 37 to the upper and lower blades 1 and 2 together. According to a further embodiment of the present invention, the upper and lower accessorial blades 36, 37 connect to the upper and lower blades 1, 2 by binder or weld. According to another embodiment of the present invention, the back of the upper accessorial blade near font of top thereof is provided with a hook for upper accessorial blade, which snaps into a limiting slot on the middle of the back-end of the upper blade so as to be fixed detachably. And/or the back of the lower accessorial blade is provided a buckle 39 for lower accessorial blade, which buckles into a limiting slot 40 on the back of the lower blade so as to be fixed detachably. Continuing to refer to FIG. 4, which further illustrates the channels 30 on the upper and lower accessorial blades 36, 37, which is composed of the channel body 31 and the channel cover 34. The size and shape of the channel body 31 are designed such that the longitudinal is longer than the transverse, the section is of U shape, inverted Π shape, or circle of a frustum. At least a hole 35 (shown respectively two in the figure) are arranged on the sides facing the vagina of the channel bodies 31 of the upper and lower accessorial blades 36, 37. The axial front end of the channel body 31 can be closed or opened, an opening 33 is arranged on the back end and connects with a pipe 32 (showed in dotted line in the figure). A slot, which is used for receiving the channel covers 34, is arranged on periphery corresponding to the holes 35. The channel cover 34 is long and thin and has the same shape as the groove on the channel bodies 31. When the channel cover 34 is embedded into the groove of the channel body, the channel is formed so as to constitute a passageway. The passageway includes the holes 35 on the channel body, the channel body 31, the channel cover 34 and the opening 33 on the back end of the channel body. When the channel 30 is used for exhausting smoke, the smoke enters into the holes 35, passes through the above passageway, to pipe 32 and then exhausts from the negative pressure device (not shown) connecting to the pipe. When having need to install a lighting or camera devices, the operator can open the channel cover, then accurately, rapidly and conveniently installs LED light or camera into holes 35 on the channel body 31 under look in the eye, make the supply lines or signal lines pass through channel 30, opening 33 on the channel body 31 and connect to outside.

According to an embodiment of the present invention, the channel body 31 of the channel and the upper and lower accessorial blades 36, 37 can be formed together by injection molding or stamping.

According to an embodiment of the present invention, the upper and lower accessorial blades 36, 37 and the channel body 31 can be formed respectively and then connected together by bonding or weld.

The vaginal dilator of the present invention can be made by stainless steel, plastics, environmental protection material or similar material, but not limited hereto.

The above specific description about the conception and embodiments of the present invention has been made. However, the technicians in the art can make various modifications and improvements based thereon, these modifications and improvements do not depart from the spirit of the present invention and all are within the protection scope defined by claims.

The invention claimed is:

1. A vaginal dilator, comprising:
    two side blades;
    an upper blade;
    a pressing member integrated with the upper blade and extending from a side of the upper blade;
    a lower blade;
    a handle integrated with the lower blade and extending from a side of the lower blade, wherein the upper and lower blades are connected by pins such that a front portion of the vaginal dilator includes the upper and lower blades and a rear portion of the vaginal dilator includes the pressing member and the handle, wherein the pressing member and the handle are engageable by a first dilating fixation device, thereby holding the upper and lower blades open from each other;
    an arc-shaped movable locating sleeve, wherein two ends of the locating sleeve are connected to a rear portion of the upper blade by sleeve-pins; and
    a mounting base provided on each end of the locating sleeve, wherein each of the mounting bases includes a mounting hole for receiving a joint axle member of one of the side blades, and wherein each of the side blades is pivotally retractable between the upper blade and the lower blade, wherein a rear portion of each of the side blades includes a second dilating fixation device capable of holding the side blades open from each other, the rear portion of each of the side blades being configured to engage with the upper blade.

2. The vaginal dilator according to claim 1, wherein each of the side blades has a front portion, a rear portion, and a middle portion defined between the front and rear portions, wherein the front portion is longer than the rear portion, the middle portion protrudes outwardly and includes the joint axle member disposed near the rear portion, wherein the joint axle member extends radially inward from the middle portion.

3. The vaginal dilator according to claim 2, wherein the front portion of each side blade has a duckbilled shape.

4. The vaginal dilator according to claim 2, wherein the front portion of each side blade has a rounded shape.

5. The vaginal dilator according to claim 1, wherein each of the side blades comprises a channel therein, and wherein each of the side blades include an opening on an inner side thereof at the front portion of each of the side blades.

6. The vaginal dilator according to claim 5, wherein each of the side blades comprises a channel cover engageable to cover the channel formed in each of the side blades.

7. The vaginal dilator according to claim 1, wherein a limiting-slot is provided on a rear portion of the upper blade; a limiting block is provided correspondingly inside a middle portion of the locating sleeve, wherein the limiting block is configured to limit an extent of downward rotation of the locating sleeve and the side blades.

8. The vaginal dilator according to claim 1, wherein the first dilating fixation device comprises:
    at least one locating member disposed on the pressing member and engageable with the handle.

9. The vaginal dilator according to claim 1, wherein the second dilating fixation device comprises:
    at least one first locating member on the rear portion of each of the side blades, and
    at least one second locating member on one of the back side of the upper blade and the mounting base.

10. The vaginal dilator according to claim 1, wherein the second dilating fixation device comprises a screw provided on an inner side of the rear portion of each of the side blades and extending inward, wherein the screw passes through a locating plate provided on the back side of the upper blade; the locating plate including an arc-shaped slot and can be rotated around the pins connecting the upper and lower blades which is a rotating center; and a nut provided on the screw.

11. A vaginal dilator, comprising:
    an upper blade, the upper blade having an inner side;
    a pressing member integrated with the upper blade and extending from a rear portion of the upper blade;
    a lower blade, the lower blade having an inner side facing toward the inner side of the upper blade;
    a handle integrated with the lower blade and extending from a rear portion of the lower blade, wherein rear portions of the upper and lower blades are connected by pins, the pressing member and the handle are engageable to hold the upper and lower blades open from each other by a dilating fixation device; and upper and lower accessorial blades provided on the inner sides of the upper and lower blades respectively, wherein each of the upper and lower accessorial blades includes a channel therein, and a channel cover embeddable into each of the upper and lower blades to cover the channel, wherein at least one hole is disposed on the inner sides of each of the upper and lower blades.

12. The vaginal dilator according to claim 11, wherein the rear portion of the upper accessorial blade is provided with a hook near the top portion thereof; and the upper accessorial blade is snapped into a limiting slot formed on the rear portion of the upper blade.

13. The vaginal dilator according to claim 11, wherein the outside of the upper and lower accessorial blades is provided with one or more bumps, and the inner side of the upper and lower blades is provided with one or more corresponding grooves for receiving the bumps.

14. The vaginal dilator according to claim 11, wherein a front portion of the channel is closeable and a rear portion is open; the cross section of the channel is one of a U-shape, an inverted $\pi$ shape, or a circular shape.

15. The vaginal dilator according to claim 11, wherein the dilating fixation device includes a locating hook provided on the pressing member and engageable with a locating buckle on the handle, wherein the placement of the locating hook and the locating buckle is interchangeable.

16. The vaginal dilator according to claim 11, wherein the dilating fixation device includes:
- a locating plate provided on the pressing member having an arc-shaped slot, the locating plate rotatable around the pin which connects the upper and lower blades; and
- a locating rod with a nut provided on the handle and passing through the arc-shaped slot on the locating plate.

* * * * *